United States Patent [19]

Obi et al.

[11] Patent Number: 5,158,748
[45] Date of Patent: Oct. 27, 1992

[54] AUTOMATED DISPENSING AND DILUTING SYSTEM

[75] Inventors: Hiroshi Obi; Kohei Ishida; Ei Mochida, all of Tokyo, Japan

[73] Assignee: Mochida Pharmaceutical Co., Ltd., Tokyo, Japan

[21] Appl. No.: 642,643

[22] Filed: Jan. 17, 1991

[30] Foreign Application Priority Data

Jan. 18, 1990 [JP] Japan .................................. 2-9183

[51] Int. Cl.⁵ .............................................. B01L 3/02
[52] U.S. Cl. ..................................... 422/100; 422/63; 73/863.01; 222/64; 222/320
[58] Field of Search ............................ 422/63, 99, 100; 436/47; 222/64, 320, 321; 141/83, 130, 258; 73/864.22, 863.01, 863.23, 863.24

[56] References Cited

U.S. PATENT DOCUMENTS

| | | | |
|---|---|---|---|
| 3,607,094 | 9/1971 | Beer | 141/130 X |
| 4,096,972 | 6/1978 | Bartels et al. | 141/83 X |
| 4,478,094 | 10/1984 | Salomaa et al. | 422/100 X |
| 4,574,850 | 3/1986 | Davis | 422/100 X |
| 4,800,762 | 1/1989 | Sugaya | 141/130 X |
| 4,810,659 | 3/1989 | Higo et al. | 436/180 |
| 4,983,515 | 1/1990 | Uchida | 73/864.34 |

FOREIGN PATENT DOCUMENTS

| | | |
|---|---|---|
| 0188265 | 7/1986 | European Pat. Off. . |
| 3039475 | 5/1982 | Fed. Rep. of Germany . |
| 56-164958 | 5/1980 | Japan . |
| 6264912 | 9/1985 | Japan . |
| 63109373 | 10/1986 | Japan . |
| 63-109330 | 5/1988 | Japan . |
| 63-145963 | 6/1988 | Japan .......................... 422/63 |

Primary Examiner—Jill A. Johnston
Assistant Examiner—Maureen M. Wallenhorst
Attorney, Agent, or Firm—Burns, Doane, Swecker & Mathis

[57] ABSTRACT

A system for automatically dispensing and diluting an accurate volume of a sample includes a nozzle tip removably mounted on a nozzle for collecting a predetermined volume of the sample. The nozzle includes an inner tube and an outer tube. The system also includes a sample pump for sucking and discharging the sample and the reagent into and out of the nozzle tip, a first three-way valve that is adapted to communicate the reagent bottle with the sample pump or the sample pump with the nozzle, and a plunger pump for sucking and discharging a liquid surface-detecting gas supplied from a gas source. A second three way valve is adapted to communicate the gas source with the plunger pump or the plunger pump with the nozzle, and a pressure sensor is positioned between the second three-way valve and the gas passage in the nozzle. Also, a two-way valve is positioned between the pressure sensor and the gas passage of the nozzle.

5 Claims, 3 Drawing Sheets

AUTOMATED DISPENSING AND DILUTING SYSTEM

BACKGROUND OF THE INVENTION

This invention relates to an automated system for dispensing and diluting a sample, which is capable of dispensing an accurate volume of the sample. More particularly, this invention relates to a system which is capable of collecting an accurate volume of the sample by an accurate detection of the sample liquid surface, and which is capable of introducing all of the thus collected accurate volume of the sample together with a diluting solution into the reaction vessel to thereby consistently enable an accurate volume of the sample to be dispensed.

In the fields of clinical examination, biochemistry, biotechnology, chemical analysis and the like wherein tests involving chemical reactions are frequently carried out to determine the results, various attempts have been made to automate the process of tests and measurements. In such tests and measurements, numerous types of samples each having little volume must be treated, and therefore, a step of dispensing, which involves a collection of a predetermined volume of the sample by suction, is inevitable. For example, in an immunoassay utilizing an antigen-antibody reaction, a specimen such as serum, plasma, urine and other body fluids collected from a living body is repeatedly dispensed into a number of reaction vessels, and the thus dispensed specimens are mixed or diluted with a reagent before the test results may be obtained. As described above, in the above-mentioned fields, numerous types of specimens must be repeatedly dispensed and diluted with reagents, and therefore, a number of attempts have been made to automate various steps of the dispensing.

In order to automate the dispensing step, an accurate detection of the liquid sample surface in the sample container is critical, since, in the automatic dispensing, the nozzle tip has to be inserted into the sample liquid to a predetermined depth to collect a predetermined volume of the sample into the nozzle tip. An inaccurate detection of the liquid surface in the container may result in a decreased dispensing precision. For example, when the liquid surface detected is higher than the actual surface, the depth of the nozzle tip inserted into the liquid would be decreased and air may be sucked into the nozzle tip to result in a significant decrease of the dispensing precision. On the contrary, when the liquid surface detected is lower than the actual surface and the nozzle tip is inserted into the sample solution further than the predetermined depth, an increased volume of the sample attached to the outer surface of the nozzle tip would be introduced into the reaction container, and also, the pressure exerted to the gas within the nozzle tip by the sample solution would be increased to change the gas volume within the nozzle tip to affect the volume of the sample collected. Consequently, the dispensing precision would be decreased Accordingly, various methods for detecting the liquid surface as well as the system used therefor have been proposed together with sampling and dispensing methods and the systems used therefor.

Japanese Patent Application Kokai No. 56-164958 discloses an automatic dispenser wherein a negative pressure is applied to a cylinder which is in communication with a nozzle tip, and the surface of the sample liquid is detected by using a pressure difference induced between atmosphere and the interior of the nozzle tip upon contact of the nozzle tip with the surface of the liquid sample, and thereafter, a predetermined volume of the sample is collected by using the negative pressure of the cylinder.

Japanese Patent Application Kokai No. 62-64912 discloses a dispenser wherein a collection of the liquid sample by suction is started in response to a change of the pressure within the nozzle before and after the contact of the lower end of the nozzle tip with the liquid sample surface, and the volume of the sample dispensed is determined on the bases of the pressure within the nozzle after collecting the sample for a predetermined time.

Japanese Patent Application Kokai No. 63-109330 discloses a liquid surface-detector wherein air is discharged and sucked through a nozzle by a pump, and liquid surface is detected by a change of the pressure within the nozzle upon contact of the nozzle with the liquid surface. The discharge and the suction of the liquid surface-detecting air is carried out with a suction pump used for collecting the sample.

Japanese Patent Application Kokai No. 63-109373 discloses a sampling system wherein air is discharged and sucked through a sampling nozzle by a compressor, and liquid surface is detected on the bases of a change of the pressure within the sampling nozzle upon access or contact of the sampling nozzle with the liquid surface, and thereafter, the sample solution is collected through the sampling nozzle with suction by using a plunger pump.

In the above-mentioned conventional liquid surface-detectors and the liquid dispensers, the suction of the sample liquid is carried out after the liquid surface detection by reducing the pressure of the air used for the liquid surface detection in the nozzle, cylinder, gas conduit, pump and the like to exert a negative pressure to the sample liquid to thereby suck the sample liquid into the nozzle. Since the air is a compressible fluid, pressure control during the suction is quite difficult. More illustratively, the state of the air at the completion of the sample collection may vary in accordance with the volume and the pressure of the air, and the volume of the sample liquid collected rendering an accurate control of the volume of the sample collected difficult. In particular, a consistent, repeated suction of a small volume of sample with little variation from sample to sample as well as from system to system is quite difficult to achieve with the conventional dispenser system.

Even if an accurate volume of the sample liquid were collected into the nozzle tip, the thus collected sample must be discharged into a reaction vessel such as a test tube for the subsequent reaction or measurement of, for example, concentration, and upon such a discharge, a considerable amount of the sample liquid will remain attached to the nozzle tip to make it difficult to discharge all of the sample liquid in the nozzle tip. Consequently, the volume of the sample discharged would be inaccurate. For dispensing an accurate volume of the sample, the volume of the sample collected by suction into the nozzle tip must be determined by taking into account the volume of the sample which will remain attached to the nozzle tip upon discharge of the sample from the nozzle tip, and this would require a troublesome step of preliminarily wetting the nozzle tip with the sample to be dispensed.

Furthermore, the dispenser is primarily intended for dispensing the sample. Therefore, when a dilution of the sample, in particular, an accurate dilution of the sample is required, the once dispensed sample has to be diluted with a diluting reagent by dispensing the reagent.

A system which is capable of carrying out both the dispensing and the diluting steps is commercially available. This commercially available system, however, requires a manual liquid surface-detection, which may lead to a variation in the results from sample to sample. Also, the system is not fully automated since the liquid surface detection is manually conducted.

SUMMARY OF THE INVENTION

An object of the present invention is to obviate the above-described technical problems and provide a system for fully automatically dispensing a sample in a sample container to reaction vessels or measurement vessels such as a test tube and dilute the thus dispensed sample with a reagent.

Another object of the present invention is to provide a system which is capable of accurately dispensing and diluting the sample even when the sample volume is small.

According to a first aspect of the invention, there is provided an automated system for dispensing and diluting a sample comprising

- a removable nozzle tip for collecting a predetermined volume of the sample, the nozzle tip being inserted into the sample to collect the sample by suction;
- a nozzle comprising an inner tube and an outer tube onto which said nozzle tip is removably mounted, said nozzle having a liquid passage through which a reagent flows and a gas passage through which a liquid surface-detecting gas flows, defined within the inner tube and between the inner and outer tubes, and said liquid passage and said gas passage are in communication with the interior of said nozzle tip;
- a sample pump for sucking and discharging the sample and the reagent into and out of the nozzle tip; a first three-way valve located in an array of tubings connecting said sample pump, said nozzle and a reagent bottle, said first three-way valve being switched to the side of the reagent bottle to communicate said reagent bottle with said sample pump or to the side of the nozzle to communicate said sample pump with said nozzle;
- a plunger pump for sucking and discharging a liquid surface-detecting gas supplied from a gas source;
- a second three-way valve located in an array of tubings connecting said plunger pump, said nozzle and said gas source, said second three-way valve being switched to the side of said gas source to communicate said gas source with said plunger pump or to the side of said nozzle to communicate said plunger pump with the nozzle;
- a pressure sensor provided between said second three-way valve and said gas passage in said nozzle; and
- a two-way valve provided between said pressure sensor and said gas passage of said nozzle, and in the vicinity of said nozzle.

According to a second aspect of the present invention, there is provided a system according to the first aspect of the invention further comprising

- a controller for controlling said first three-way valve, said second three-way valve and said two-way valve in response to signals from said pressure sensor; and
- a controller for controlling said sample pump and said plunger pump in response to signals from said pressure sensor.

According to a third aspect of the invention, there is provided a system according to the first or second aspect of the invention further comprising

- an X-Y table comprising a sample section wherein one or more containers accommodating said sample are aligned in rows, a nozzle tip section wherein one or more said nozzle tips are aligned in rows, and a test tube section wherein one or more test tubes into which said sample is dispensed are aligned in rows;
- a means for traveling said nozzle in vertical direction;
- an X-Y traveling means for moving said vertically traveling means in transverse X-Y directions over said X-Y table, said X-Y traveling means supporting said vertically traveling means; and
- a means for supporting said X-Y traveling means.

In the above-described three aspects of the present invention, the nozzle tip may preferably be a disposable nozzle tip, and the liquid surface-detecting gas may preferably be air.

Before explaining the embodiments of the invention in detail, it is to be understood that the invention is not limited in its application to the details of construction and the arrangement of components as set forth in the following description or as illustrated in the accompanying drawings. The invention is capable of other embodiments and of being practiced or carried out in various ways.

DESCRIPTION OF THE PREFERRED EMBODIMENT

An automated system for dispensing and diluting a sample in accordance with the present invention is hereinafter described in detail by referring to a preferred embodiment illustrated in the accompanying drawings.

Figure 1:
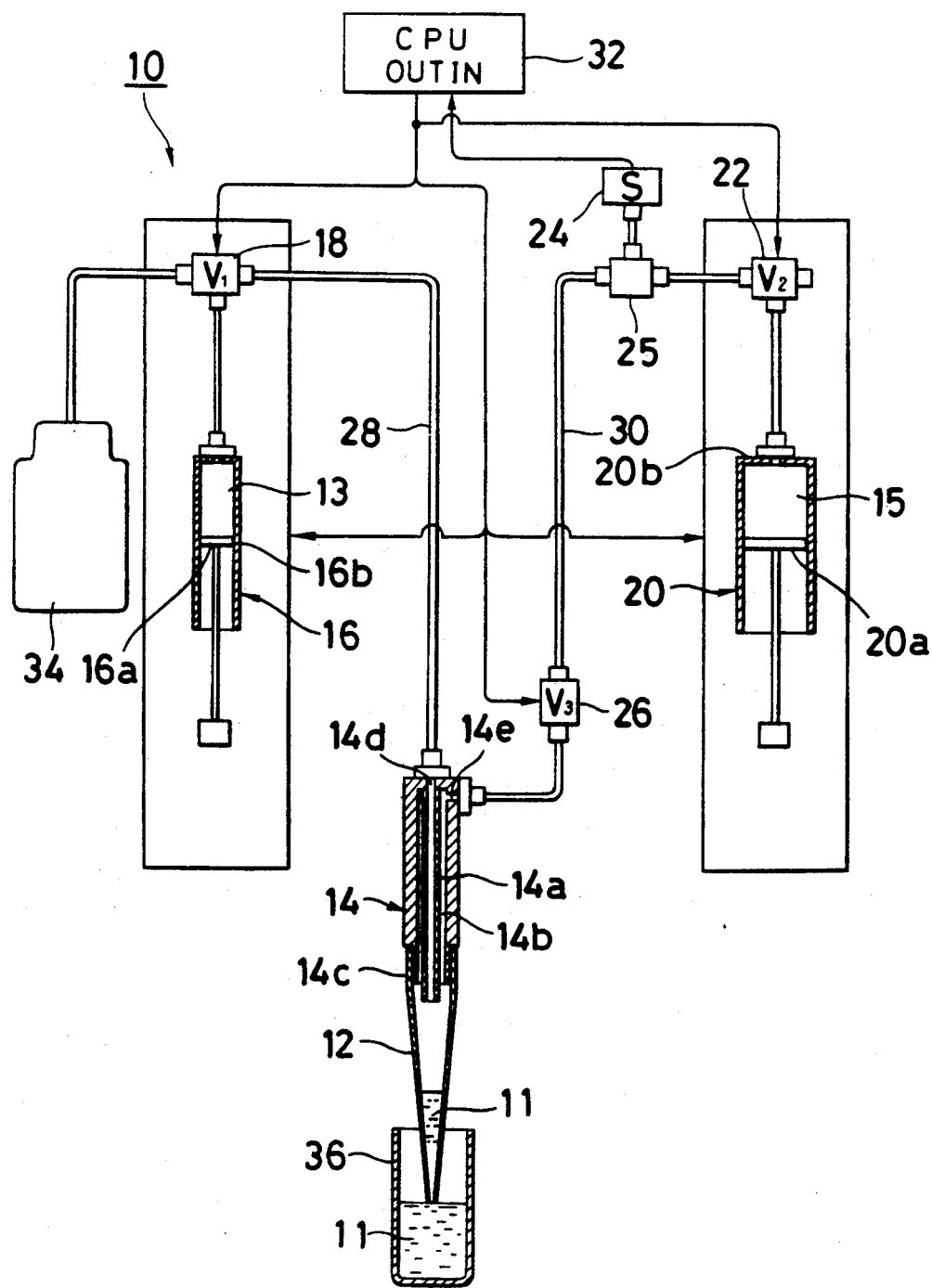
FIG. 1 is a schematic view of an automated dispensing and diluting system according to an embodiment of the present invention.

Referring to FIG. 1, there is schematically illustrated an automated dispensing and diluting system 10 according to first and second aspects of the present invention.

As shown in FIG. 1, the automated dispensing and diluting system 10 in accordance with the present invention comprises a nozzle tip 12, a nozzle 14, a sample pump 16 comprising a plunger 16a and a cylinder 16b, a first three-way valve 18, a plunger pump 20 comprising a plunger 20a and a cylinder 20b, a second three-way valve 22, a pressure sensor 24, a two-way valve 26, and flexible tubings 28 and 30. The automated dispensing and diluting system 10 may further comprise a controller 32.

The nozzle tip 12 may have any desired configuration and any desired inner volume insofar as the nozzle tip 12 is tapered at its lower end portion to hold a predetermined volume of a sample 11 therein. Preferably, the nozzle tip 12 is removably mounted onto the nozzle 14, and therefore, the nozzle tip 12 may preferably be a disposable nozzle tip. The volume of the sample 11 sucked in the nozzle tip 12 may be determined by suitably selecting the inner volume of the sample pump 16, which is defined by the plunger 16a and the cylinder 16b.

The nozzle 14 comprises an inner tube and an outer tube. A liquid passage 14a is defined within the inner tube, and a reagent 13 flows through the liquid passage 14a. A gas passage 14b is defined between the inner tube and the outer tube, and a liquid surface detecting gas 15, which is preferably air, flows through the gas passage 14b. The outer tube 14 is provided with a nozzle tip-mounting portion 14c at its lower end. The nozzle 14 is provided at its upper end with an inlet 14d for the liquid passage 14a and an inlet 14e for the gas passage 14b. As described above, the nozzle tip 12 is removably mounted on the nozzle 14 at the nozzle tip-mounting portion 14c. For the purpose of attaining a high precision, the nozzle tip 12 is air-tightly mounted to the nozzle 14.

The sample pump 16, which comprises the plunger 16a and the cylinder 16b, is provided for the suction and the discharge of a predetermined volume of the sample 11 as well as a predetermined volume of reagent 13. The sample pump 16 first sucks a predetermined volume of the reagent 13 from a reagent bottle 34 by the downward movement of the plunger 16a in relation to the cylinder 16b, and fills the first three-way valve 18, the flexible tube 28, and the liquid passage 14a of the nozzle 14 with the reagent 13 by the upward movement of the plunger 16a in relation to the cylinder 16b. The sample pump 16 then actuates to suck the sample 11 in the sample container 36 into the nozzle tip 12 and to discharge the sample 11 from the nozzle tip 12 into a test tube 54 by the downward and upward movements of the plunger 16a in relation to the cylinder 16b. The suction and the discharge of the sample 11 into and out of the nozzle tip 12 is carried out via the reagent 13 within the tubing and the liquid passage 14a of the nozzle 14 and the liquid surface-detecting gas 15 within the nozzle tip 12. After the discharge of the sample 11 from the nozzle tip 12, the sample pump 16 may actuate to drop a predetermined volume of the reagent 13 onto the interior of the tapered lower end portion of the nozzle tip 12 to wash off the sample 11 remaining in the nozzle tip 12. The sample 11 is thereby dispensed and diluted with the reagent 13. For the purpose of achieving a more complete discharge of the sample 11 and the reagent 13 from the nozzle tip 12, the plunger pump 20 may be actuated to discharge the gas 15, preferably the air, from the gas passage 14b of the nozzle 14 to completely discharge both the liquids remaining at the lower end of the nozzle liquid passage 14a and the liquids remaining on the interior and at the lower end of the nozzle tip 12.

The first three-way valve 18 is situated in an array of tubings connecting the sample pump 16, the nozzle 14 and a reagent bottle 34. The first three-way valve 18 may be switched to the side of the reagent bottle 34 to allow the reagent 13 to flow from the reagent bottle 34 to the sample pump 16, or to the side of the nozzle 14 to allow the reagent to flow through the passage from the sample pump 16 to the nozzle 14. When the reagent 13 is freshly sucked into the sample pump 16, the first three-way valve 18 terminates the flow of the reagent 13 from the sample pump 16 to the nozzle 14 and communicates the reagent bottle 34 with the sample pump 16. During the suction and the discharge of the sample 11 into and out of the nozzle tip 12 and the discharge of the reagent 13 from the nozzle tip 12, the first three-way valve 18 terminates the flow of the reagent 13 from the reagent bottle 34 to the sample pump 16 and communicates the sample pump 16 and the liquid passage 14a of the nozzle 14.

The plunger pump 20 comprises the plunger 20a and the cylinder 20b. The plunger pump 20 is provided for two major purposes. First, the plunger pump 20 actuates to discharge the liquid surface-detecting gas 15 from the nozzle tip 12 so that, upon contact of the lower end of the downward moving nozzle tip 12 with the liquid surface, the pressure of the liquid surface-detecting gas 15 within the nozzle tip 12 is increased and the pressure sensor 24 detects this pressure increase. Secondly, the plunger pump 20 actuates to discharge the gas 15 from the gas passage 14b for the purpose of a complete discharge of the sample 11 and the reagent 13 remaining at the lower end of the nozzle tip 12 after the discharge of the sample 11 and the reagent 13.

The second three-way valve 22 is located in an array of tubings connecting the plunger pump 20, the nozzle 14 and a gas source (not shown). The second three-way valve 22 may be switched to the side of the gas source such as atmosphere to allow for the gas 15, which is typically air, to flow from the gas source to the plunger pump 20, or to the side of the nozzle 14 to allow the gas to flow from the plunger pump 20 to the nozzle 14. When the gas 15 is freshly sucked into the plunger pump 20, the second three-way valve 22 terminates the flow of the gas 15 from the plunger pump 20 to the nozzle 14 and communicates the gas source, typically atmosphere, with the plunger pump 20. During the discharge of the gas 15 from the nozzle tip 12 for the detection of the liquid surface or the complete removal of the liquids remaining attached to the nozzle tip 12, the second three-way valve 22 terminates the flow of the gas from the gas source or atmosphere to the plunger pump 20 and communicates the plunger pump 20 with the gas passage 14b of the nozzle 14.

The pressure sensor 24 is provided between the second three-way valve 22 and the two-way valve 26 for the purpose of measuring a pressure deviation of the liquid surface-detecting gas. The type of the pressure sensor 24 is not particularly limited insofar as it can detect the pressure exerted by the plunger pump 20 upon contact of the lower end of the nozzle tip 12 with the surface of the sample 11 resulting in a blockage of the gas passage from the nozzle tip 12, the gas passage 14b of the nozzle 14, the two-way valve 26, the flexible tube 30, the second three-way valve 22, and the plunger pump 20. Any pressure sensor of known type may be used including those measuring an absolute pressure and a gauge pressure (differential pressure), and those capable of producing a signal indicating the detection of the liquid surface by changing an electric output signal at a predetermined pressure. Exemplary pressure sensors include a strain gauge, a semiconductor gauge, and a piezo element.

The two-way valve 26 is an on-off valve, and is provided between the pressure sensor 24 and the nozzle 14, and in the vicinity of the inlet 14e of the gas passage 14b. The two-way valve 26 is closed except for during the detection of the liquid surface and during the complete discharge of the sample and the reagent remaining attached to the nozzle tip 12.

The flexible tube 28 connects the first three-way valve 18 and the inlet 14d of the liquid passage 14a of the nozzle 14. The flexible tube 30 connects the two-way valve 26 and a T coupler 25 onto which the pressure sensor 24 is connected. Since the nozzle 14 travels both in the vertical direction, namely the Z direction and in transverse directions, namely X-Y directions as will be described later, the tubes 28 and 30 may preferably have a sufficient length as well as a sufficient flexibility to avoid excess elongation of the tube and to prevent the tube from being folded to result in the blockage of the tube.

As described above, the automated dispensing and diluting system of the present invention comprises a liquid surface-detecting system and a dispensing/diluting system.

Among the components described above, the plunger pump 20, the second three-way valve 22, the pressure sensor 24, the tube 30, the two-way valve 26, the gas passage 14b of the nozzle 14, and the nozzle tip 12 constitute the liquid surface-detecting system.

On the other hand, the sampling pump 16, the first three-way valve 18, the tube 28, the liquid passage 14a of the nozzle 14, and the nozzle tip 12 constitute the dispensing/diluting system.

The most characteristic feature of the automated dispensing and diluting system 10 in accordance with the present invention resides in that the suction of the sample 11 by the sample pump 16 is carried out mainly through the reagent 13 while the two-way valve 26 is closed. In the present system, the gas or the air, which is a fluid susceptible to compression, is present only within the nozzle tip 12, the gas passage 14b of the nozzle 14, and the tubing between the inlet 14e of the gas passage 14b and the two-way valve 26, and the suction of the sample 11 is thus carried out mainly through the reagent 13, which is a non-compressible liquid. Accordingly, the pressure of the gas 15 within the nozzle tip 12 at the time of the suction as well as the volume of the sample 11 sucked into the nozzle tip 12 can be readily and accurately controlled. Furthermore, since the sample 11 sucked into the nozzle tip 12 is first discharged by the pressure exerted by the sample pump 16, and then washed off by the reagent 13 dripping onto the interior surface of the tapered lower end portion of the nozzle tip 12, and finally blown off by the gas supplied by the plunger pump 20, the volume of the sample discharged is accurate to consistently ensure an accurate volume of the sample to be dispensed.

The controller 32 controls the motion of the first three way valve 18, the second three-way valve 22 and the two-way valve 26, and the vertical movement of the nozzle 14 in the Z direction as well as their relative movements in response to the signal from the pressure sensor 24 produced on the bases of the pressure of the liquid surface-detecting gas. The controller 32 may comprise a central processing unit. The controller 32 may also control the timing, the volume and the speed of the suction/discharge of the sample pump 16 and the plunger pump 18, and further, the three dimensional movements of the nozzle 14 in the X, Y and Z directions. The control of the pumps 16 and 20 and the control of the nozzle 14 may be accomplished separately from the control of the valves 18, 22 and 26 by providing additional controllers.

The construction of the automated dispensing and diluting system in accordance with the first and the second aspects of the present invention has been described in the foregoing. An automated dispensing and diluting system in accordance with the third aspect of the invention is illustrated in FIG. 2.

Figure 2:
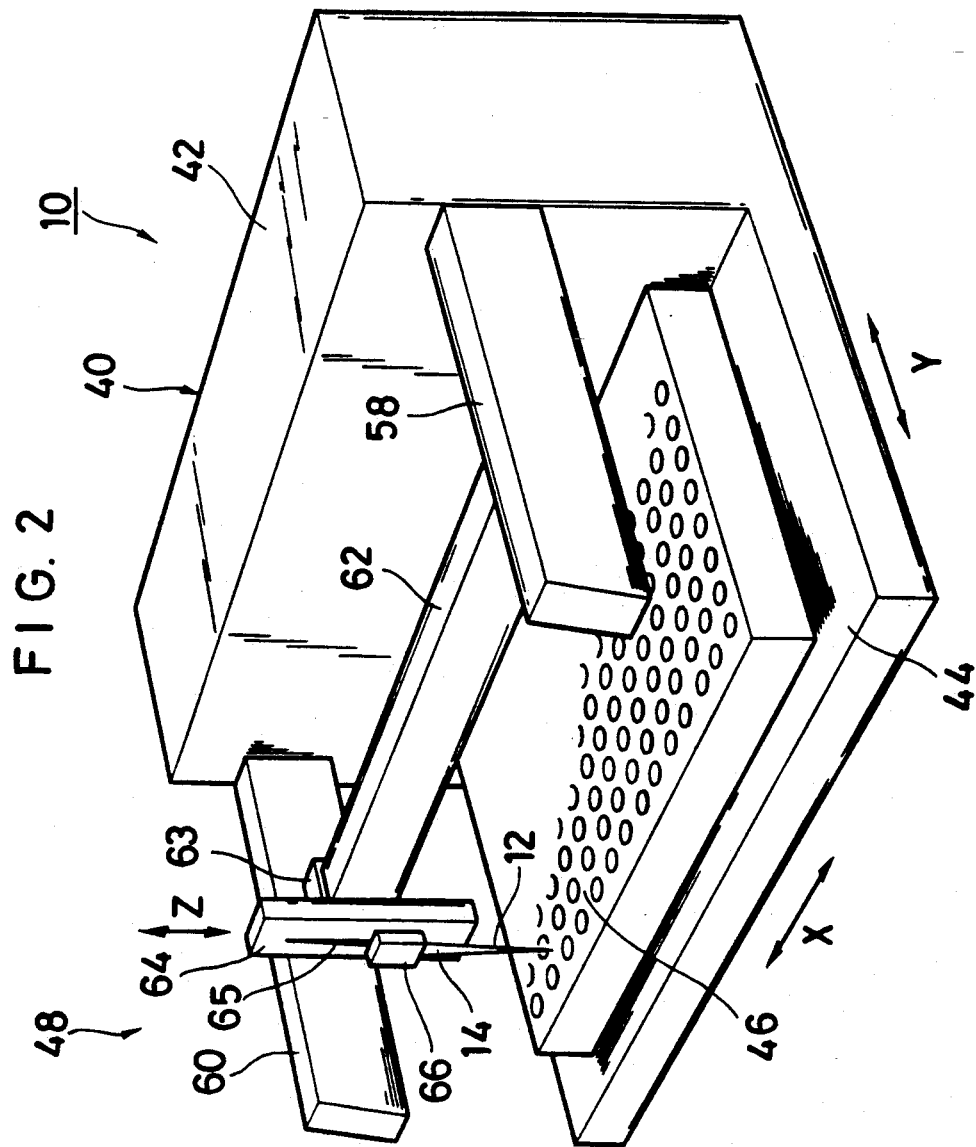
FIG. 2 is a perspective view of an automated dispensing and diluting system according to an embodiment of the present invention.

The automated dispensing and diluting system 10 shown in FIG. 2 comprises a section 42 for accommodating the above-described components, and a base 44 extending in the horizontal direction from the bottom of the accommodating section 42, said accommodating section 42 and said base constituting a main part 40 of the system, and X-Y table 46 disposed on the base 44, a nozzle-traveling means 48 for moving said nozzle 14 over the X-Y table 46 in the X, Y and Z directions.

Figure 3:
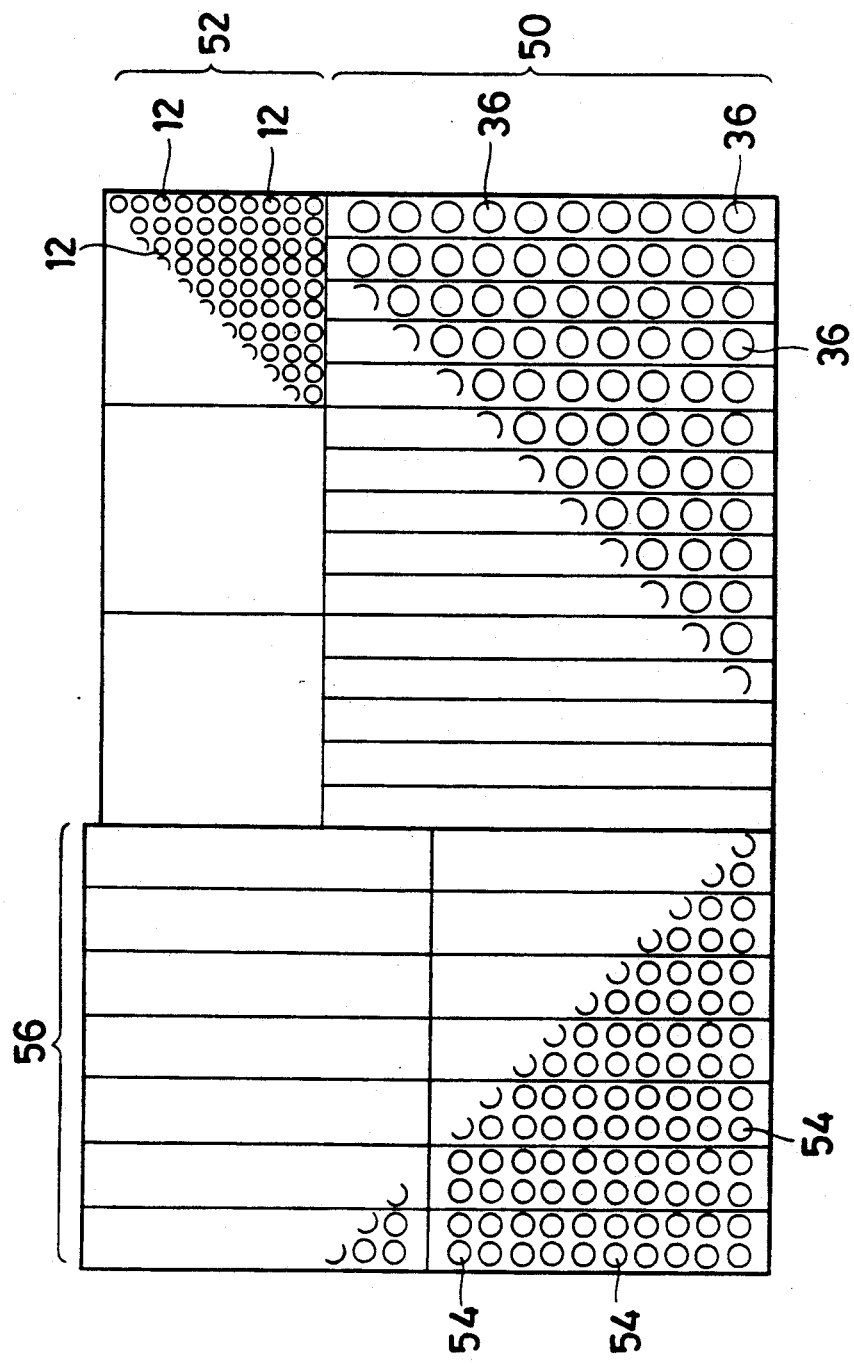
FIG. 3 is a top plan view of an X-Y table employed in the automated dispensing and diluting system according to an embodiment of the present invention.

Referring to FIG. 3, the X-Y table 46 comprises a sample section 50 wherein one or more sample specimen containers 36 accommodating said sample specimen 11 are aligned in rows, a nozzle tip section 52 wherein one or more of said nozzle tips 12 are aligned in rows, and a test tube section 56 wherein one or more test tubes 54, into which the sample 11 and the reagent 13 are dispensed, are aligned in rows.

The nozzle-traveling means 48 comprises two beams 58 and 60 extending in the forward or Y direction from the forward surface of the accommodating section 42 at its top and on opposite ends; an arm 62 supported between the two beams 58 and 60 extending perpendicularly to the beams 58 and 60 in the X direction, the arm 62 being capable of traveling in the Y direction; a clamp 63 movably grasping the arm 62 and a plate 64 mounted on the clamp 63, the clamp 63 and the plate 64 being capable of traveling in the X direction; a nozzle-supporting member 66 movably mounted on the plate 64, the nozzle-supporting member 66 being capable of traveling in the Z direction along a guide 65 provided in the plate 64; and a drive (not shown).

Onto the nozzle-supporting member 66 is mounted the nozzle 14, and the nozzle tip 12 is removably mounted to the nozzle 14. In FIG. 2, various components shown in FIG. 1 are not shown except for the nozzle 14 and the nozzle tip 12, and the components other than the nozzle 14 and the nozzle tip 12 are either accommodated in the accommodating section 42 or abbreviated for drawing convenience.

The plate 64 extends vertically, and the guide 65 is provided in the plate 64 along its longitudinal axis. The plate 64, the guide 65, the nozzle-supporting member 66, and the drive (not shown) constitute a means for traveling the nozzle 14 in the vertical direction.

The plate 64 is fixedly secured to the clamp 63. The clamp 63, the arm 62 and the drive (not shown), which is typically a wire drive, constitute a means for traveling the nozzle 14 in the X direction. The arm 62, the beams 58 and 60, and the drive (not shown), which is also typically a wire drive, constitute a means for traveling the nozzle 14 in the Y direction. These means for traveling the nozzle 14 in the X and Y directions constitute a means for traveling the nozzle in the X-Y directions. The nozzle-traveling means 48 comprises the X-Y traveling means and the vertically traveling means.

The drive (not shown) of the nozzle-traveling means 48 may comprise any conventional drive of known type, such as a wire with a pulley, a rack with a pinion, or the like.

The sample which may be used in the present invention is not limited to any particular type. The samples used are preferably those used in immunoreactions such as serum, plasma, urine, and other body fluids.

The reagents which may be used in the present invention are, for example, purified water for dilution, and reagents which will be required in the subsequent reaction and which may be added beforehand. Typical reagents used are physiological saline and a buffer solution having bovine serum albumin added thereto.

The liquid surface-detecting gas used in the present invention is not limited to any particular type insofar as the gas is inert with the sample specimen and the reagent, and is capable of transmitting a minute change of pressure. Exemplary gases include air, nitrogen gas, and other inert gases, among which the air being the most preferable for its low cost requiring no special installation.

The automated dispensing and diluting system in accordance with the present invention is an important unit which constitutes an immunological measurement system together with an immunoreaction apparatus and a measuring apparatus. The present system may automatically and accurately dispense the sample into the test tubes and dilute the thus dispensed sample with the reagents, so that an immunoreaction may take place within the test tube in the immunoreaction apparatus.

The automated dispensing and diluting system of the present invention basically has a construction as set forth above. The operation of the automated dispensing and diluting system of the present invention is hereinafter described.

At first, the nozzle 14 of the automated dispensing and diluting system 10 is at its home position. The nozzle tip 12 is not yet mounted.

When a start switch is turned on, the arm 62 and the clamp 63 shown in FIG. 2 travel in transverse directions, that is, X and Y directions over the X-Y table 46 to the nozzle tip section 52 of the X-Y table 46 shown in FIG. 2. The nozzle 14 stops at the nozzle tip-mounting position. The nozzle 14 then moves downward along the guide 65 so that the nozzle tip 12 is mounted to the nozzle 14.

After completion of the mounting of the nozzle tip 12 onto the nozzle 14, the nozzle 14 together with the nozzle tip 12 moves upward along the guide 65 to the uppermost position of the guide 65.

Next, the nozzle 14 again travels over the X-Y table 46 by the X-Y traveling means to the sample section 50 of the X-Y table 46, and stops at the sample collecting position upon the sample container 36.

By this moment, the plunger pump 20 has already sucked a predetermined volume of the air 15 therein, and the second three-way valve 22 has been switched to the nozzle side to allow the air to flow from the plunger pump 20 to the nozzle 14. The two-way valve 26 has been opened. The sample pump 16 has already sucked a predetermined volume, for example, 200 µl of the reagent 13 therein, and the first three-way valve 18 has been switched to the nozzle side to allow the reagent 13 to flow through the passage between the sample pump 16 and the nozzle 14. The liquid passage has been filled with the reagent 13.

Next, the nozzle 14 starts to move downward by the vertically traveling means. At the same time, the plunger pump 20 actuates to discharge the air 15 within the cylinder 20b by the upward movement of the plunger 20a. The air 15 discharged from the plunger pump 20 flows through the second three-way valve 22, the pressure sensor 24, the two-way valve 26, the gas passage 14b, and the nozzle tip 12, and is discharged from the lower end of the nozzle tip 12.

When the lower end of the nozzle tip 12 contacts the surface of the sample 11, the pressure within the nozzle tip 12 is increased. The pressure sensor 24 then detects this pressure increase.

When the pressure sensor 24 detects a predetermined level of the pressure increase, it outputs a signal to indicate that the liquid surface has been detected. When this liquid surface-detection signal is output by the pressure sensor 24, the plunger pump 20 stops its motion to terminate the discharge of the air 15, and consequently the pressure increase is ceased.

Immediately after the liquid surface detection, counting is started to allow the nozzle to move downward a predetermined distance from the position at which the liquid surface has been detected before the nozzle 14 is stopped. The lower end of the nozzle tip 12 is then located the predetermined distance, for example, 2 to 3 mm, below the liquid surface. The predetermined distance is determined in accordance with the volume of the sample 11 to be dispensed and the size of the sample container 36.

Next, the two-way valve 26 is closed and the three-way valve 22 is switched to the atmosphere side so that the plunger pump is in communication with the atmosphere.

The sample pump 16 then actuates to suck a predetermined volume, for example, 50 µl of the sample 11 into the nozzle tip 12 by the downward motion of the plunger 16a in relation to the cylinder 16b. In the meanwhile, the plunger pump 20 sucks in a predetermined volume of the air 15 from the atmosphere side.

Upon the completion of the sucking of the sample 11 into the nozzle tip 12, the nozzle 14 moves upward along the guide 65 and stops at the uppermost position of the guide 65. The nozzle 14 then travels over the X-Y table by the X-Y traveling means to the test tube section 56 of the X-Y table 46. The nozzle 14 stops at the discharge position upon the predetermined test tube 54.

Next, the nozzle 14 moves downward to a predetermined position, for example, in the vicinity of the inlet of the test tube 54.

The sample pump 16 then actuates and the plunger 16a moves upward, for example, to the uppermost end of the cylinder 16b to first discharge the sample 11 in the nozzle tip 12 and then to wash off the sample 11 remaining in the nozzle tip 12 with the reagent 13, which is discharged from the liquid passage 14a of the nozzle 14 to drop onto the interior of the tapered lower end portion of the nozzle tip 12.

After the discharge of the predetermined volume of the reagent 13 from the nozzle tip 12, the sample pump 16 stops its motion, the first three-way valve 18 is switched to the side of the reagent container 34, the second three-way valve 22 is switched to the side of the nozzle 14, and the two-way valve 26 is opened. The plunger pump 20 then actuates with the upward movement of the plunger 20a to discharge the air 15 from the nozzle tip 12 to completely discharge the sample 11 and the reagent 13 remaining at the lower end of the nozzle tip 12. Upon the completion of the discharge of the remaining liquids, the second three-way valve 22 is again switched to the atmosphere side.

The sample pump 16 and the plunger pump 20 then actuate to suck the predetermined volume, for example, 200 µl of the reagent 13 and the air 15, respectively, by the downward motion of the plungers 16a and 20a. After sucking, the pumps 16 and 20 stop their motion.

Both the first three-way valve 18 and the second three-way valve 22 are switched to the side of the nozzle 14.

Next, the nozzle 14 moves upward along the guide 65 to stop at the uppermost position of the guide 65.

Next, the nozzle 14 travels over the X-Y table 46 to the nozzle tip removing position by the X Y traveling means to remove the nozzle tip 12 from the nozzle 14. The nozzle 14 then returns to its home position. Now, the system is prepared for the next dispensing operation.

An accurate, consistent dispensing/dilution may be realized by repeating the process as described above.

EFFECT OF THE INVENTION

As described above, in the present invention, the volume of the liquid surface-detecting gas used is minimized by the use of the nozzle comprising the inner and the outer tubes and by the suction of the sample specimen into the nozzle tip by means of the purified water or the reagent used for dilution in order to realize a convenient pressure control during the suction to thereby establish a consistent, accurate suction volume.

According to the present system, cross-contamination of the specimens are completely avoided by using the disposable tips.

Furthermore, according to the present system, the accurate volume of the sample sucked into the nozzle tip is washed out with the diluting reagent, and the liquids (the sample and the reagents) remaining attached on the lower end of the nozzle tip are blown off by the liquid surface-detecting gas, which is typically the air, and therefore, a consistent, accurate volume of the sample may be dispensed. As a consequence, variation from system to system or user to user may be reduced to an extremely low level.

Still further, the system of the present invention enables a complete automation of the dispensing as well as the dilution with an accurate diluting volume to significantly simplify the measurement process.

We claim:

1. An automated system for dispensing and diluting a sample comprising
   a removable nozzle tip for collecting a predetermined volume of the sample, the nozzle tip being inserted into the sample to collect the sample by suction;
   a nozzle comprising an outer tube onto which said nozzle tip is removably mounted and an inner tube disposed in said outer tube, said nozzle having a liquid passage defined within the inner tube for allowing a reagent to flow therethrough and a gas passage defined between the inner tube and the outer tube for allowing a liquid surface-detecting gas to flow therethrough, said liquid passage and said gas passage being in communication with an interior of said nozzle tip;
   a sample pump for sucking and discharging reagent into and out of the sample pump and for sucking and discharging the sample into and out of the nozzle tip, said suction and discharge of the sample being mediated by the reagent;
   a first three-way valve located in an array of tubings connecting said sample pump, said nozzle and a reagent bottle, said first three-way valve being switchable between one position for communicating said reagent bottle with said sample pump and another position for communicating said sample pump with said nozzle;
   a plunger pump adapted to be connected to a gas source for sucking and discharging a liquid surface-detecting gas supplied from the gas source;
   a second three-way valve located in an array of tubings connecting said plunger pump, said nozzle and said gas source, said second three-way valve being switchable between one position for communicating said gas source with said plunger pump and another position for communicating said plunger pump with the nozzle;
   a pressure sensor provided between said second three-way valve and said gas passage in said nozzle to produce a signal upon detection of a change in gas pressure within the gas passage caused by contact or access of said nozzle tip with a surface of the sample liquid; and
   a two-way valve positioned adjacent the nozzle at a position between said pressure sensor and said gas passage in said nozzle, said two-way valve being positioned closer to said nozzle than to said pressure sensor.

2. The system according to claim 1 wherein said removable nozzle tip is a disposable tip.

3. The system according to claim 1 wherein said liquid surface-detecting gas is air.

4. The system according to claim 1 further comprising
   a controller for controlling said first three-way valve, said second three-way valve and said two-way valve in response to the signal produced by said pressure sensor; and
   a controller for controlling said sample pump and said plunger pump in response to the signal produced by said pressure sensor.

5. The system according to any of the foregoing claims further comprising
   an X-Y table that includes a sample section wherein one or more containers accommodating said sample are aligned in rows, a nozzle tip section wherein one or more of said nozzle tips are aligned in rows, and a test tube section wherein one or more test tubes into which said sample is dispensed are aligned in rows, said sample section, said nozzle tip section and said test tube section defining independent sections on the X-Y table;
   vertically traveling means for traveling said nozzle in a vertical direction;
   X-Y traveling means for traveling said vertically traveling means in transverse X-Y directions over said X-Y table, said X-Y traveling means supporting said vertically traveling means; and
   means for supporting said X-Y traveling means to suspend the nozzle with its vertically traveling means and X-Y traveling means over the X-Y table.

* * * * *